United States Patent [19]
Xavier et al.

[11] Patent Number: 6,063,121
[45] Date of Patent: May 16, 2000

[54] VERTEBRAL BODY PROSTHESIS

[76] Inventors: Ravi Xavier; Samantha Xavier; Shaun Xavier, all of 748 Lakeside Dr., North Palm Beach, Fla. 33408

[21] Appl. No.: 09/124,495

[22] Filed: Jul. 29, 1998

[51] Int. Cl.[7] .................................................. A61F 2/44
[52] U.S. Cl. ........................................ 623/17; 606/61
[58] Field of Search ................................ 623/16, 17, 18; 606/60, 61

[56] References Cited

U.S. PATENT DOCUMENTS

| | | | |
|---|---|---|---|
| 3,867,728 | 2/1975 | Stubstad et al. | 623/17 |
| 4,553,273 | 11/1985 | Wu | 623/18 |
| 5,236,460 | 8/1993 | Barber | 623/17 |
| 5,246,458 | 9/1993 | Graham | 623/17 |
| 5,360,430 | 11/1994 | Lin | 606/61 |
| 5,458,641 | 10/1995 | Ramirez Jimenez | 623/17 |
| 5,480,442 | 1/1996 | Bertagnoli | 623/17 |
| 5,534,030 | 7/1996 | Navarro et al. | 623/17 |
| 5,556,431 | 9/1996 | Büttner-Janz | 623/17 |
| 5,562,738 | 10/1996 | Boyd et al. | 623/17 |
| 5,645,599 | 7/1997 | Samani | 623/17 |
| 5,658,335 | 8/1997 | Allen | 623/17 |
| 5,674,296 | 10/1997 | Bryan et al. | 623/16 |
| 5,676,701 | 10/1997 | Yuan et al. | 623/17 |
| 5,676,702 | 10/1997 | Ratron | 623/17 |
| 5,683,465 | 11/1997 | Shinn et al. | 623/17 |
| 5,702,450 | 12/1997 | Bisserie | 623/17 |
| 5,702,453 | 12/1997 | Rabbe et al. | 623/17 |
| 5,782,832 | 7/1998 | Larsen et al. | 623/17 |
| 5,893,889 | 4/1999 | Harrington | 623/17 |
| 5,895,428 | 4/1999 | Berry | 623/17 |
| 5,899,941 | 5/1999 | Nishijima et al. | 623/17 |

*Primary Examiner*—Michael J. Milano
*Assistant Examiner*—Tram A. Nguyen
*Attorney, Agent, or Firm*—Kenneth W. Iles

[57] ABSTRACT

An upper plate includes a depending truncated cone member that supports a ball. A lower plate supports an upstanding truncated cone member that supports a cup socket that the ball is press fitted into. The cup socket embraces the ball to a line above the middle diameter of the ball to prevent the ball from coming free of the socket in normal use. A number of wires form a repeating X pattern between the upper and lower plates about their perimeters and serve to restrain rotational motion. The upper plate includes upwardly projecting spikes and the lower plate includes downwardly projecting spikes. The upper and lower plates each include two anchoring brackets that project outwardly to lie adjacent to an upper and lower spinal disc, and that are fastened to the discs by bone screws. The spikes further anchor the vertebral body prosthesis in the adjacent spinal discs.

12 Claims, 3 Drawing Sheets

VERTEBRAL BODY PROSTHESIS

BACKGROUND OF THE INVENTION

1. Field of the Invention

The present invention is related to an apparatus for stabilizing the spine when spinal discs have deteriorated. More particularly, the present invention is related to an apparatus for replacing damaged spinal discs and vertebral bodies.

2. Description of Related Art Including Information Disclosed Under 37 C.F.R. Sections 1.9–1.99.

The spine, particularly the human spine, is composed of many vertebral bones stacked one upon the other, with an intervertebral disc between each pair of adjacent vertebral bones. The discs act as cartilaginous cushions and shock absorbers. The spinal cord runs in a bony canal formed by successive openings in these bones. The spinal nerves exit the spinal cord from small openings in the vertebral bodies and supply nerves and nerve signals to and from other body structures.

Damage to the structure of this system may arise from several causes. Accidental fractures of the bones leads to disruption and collapse of spinal discs and hence pinching of important nerves in the spinal cord. Collapsed, herniated or bulging discs can also pinch the nerves in the spinal cord or nerves exiting the spinal cord. Post operative scarring often lead to disruption of the spinal cord and associated structures.

Surgery is often required to reconstruct the vertebral bodies, remove the herniated discs, and to implant certain hardware to stabilize the spine. Such hardware typically comprises rods, screws, and plates. A scaffolding is formed to lift and hold the bony structures formed by the vertebral bones. Unfortunately, many of these hardware structures fail when they lose bony purchase, pierce unwanted structures, and so forth. Further, many of these structures unnecessarily limit the patient's range of spinal motion, particularly rotational movement. Many such structures, for example, the spine discs disclosed in U.S. Pat. Nos. 5,676,702, 5,645,599 and 5,702,450, tend to deteriorate over time and so cannot be considered permanent.

Therefore, a need exists for a vertebral body prosthesis that does not lose bony purchase over time, that does not unnecessarily limit the patient's range of spinal motion, particularly rotational movement, and that is stable over a long period of time.

SUMMARY OF THE INVENTION

Accordingly, it is a primary object of the present invention to provide a vertebral body prosthesis that does not lose bony purchase over time.

It is another object of the present invention to provide a vertebral body prosthesis that does not unnecessarily limit the patient's range of spinal motion, particularly rotational movement.

It is another object of the present invention to provide a vertebral body prosthesis that is stable over a long period of time.

These and other objects of the present invention are achieved by providing an upper plate having a depending truncated cone member that supports a ball. A lower plate supports an upstanding truncated cone member that supports a cup socket that the ball is press fitted into. The cup socket embraces the ball to a line above the middle diameter of the ball to prevent the ball from coming free of the socket in normal use. A number of wires form a repeating X pattern between the upper and lower plates about the perimeter of the plates and serve to restrain rotational motion. The upper plate includes upwardly projecting spikes and the lower plate includes downwardly projecting spikes. The upper and lower plates each include two anchoring brackets that project outwardly to lie adjacent to an upper and lower vertebral bodies and that are fastened to the vertebral bodies by bone screws. The spikes further anchor the vertebral body prosthesis in the adjacent spinal discs or the vertebral body surfaces after removing the damaged disc.

Other objects and advantages of the present invention will become apparent from the following description taken in connection with the accompanying drawings, it is set forth by way of illustration and example, the preferred embodiment of the present invention and the best mode currently known to the inventor for carrying out his invention.

DETAILED DESCRIPTION OF THE PREFERRED EMBODIMENTS

Figure 1:
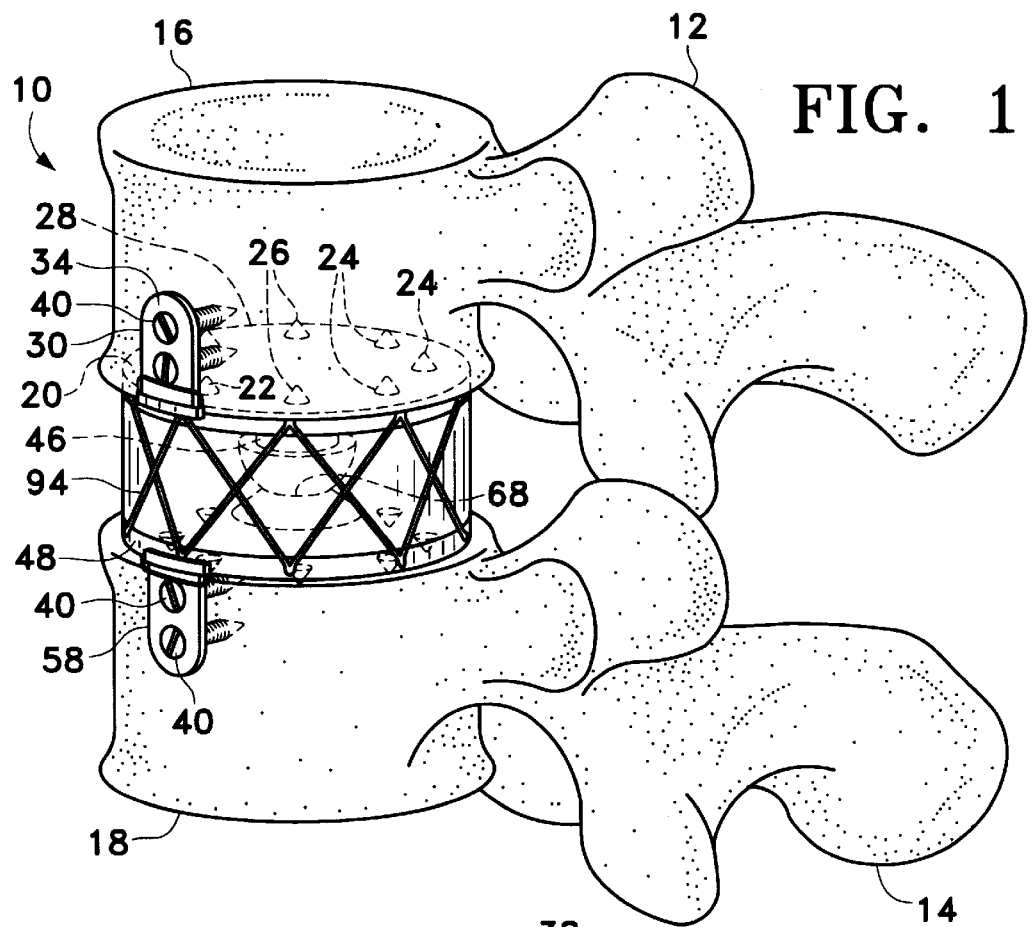
FIG. 1 is a side elevation of a vertebral body prosthesis according to the present invention showing the invention in place in a person's spine.

Referring to FIG. 1, a vertebral body prothesis 10 according to the present invention is show in place between an upper vertebra 12 and a lower vertebra 14. The upper vertebra 12 includes an associated upper elastic fibrous disc 16 and a lower elastic fibrous disc 18 is included in the lower vertebra 14.

Figure 2:
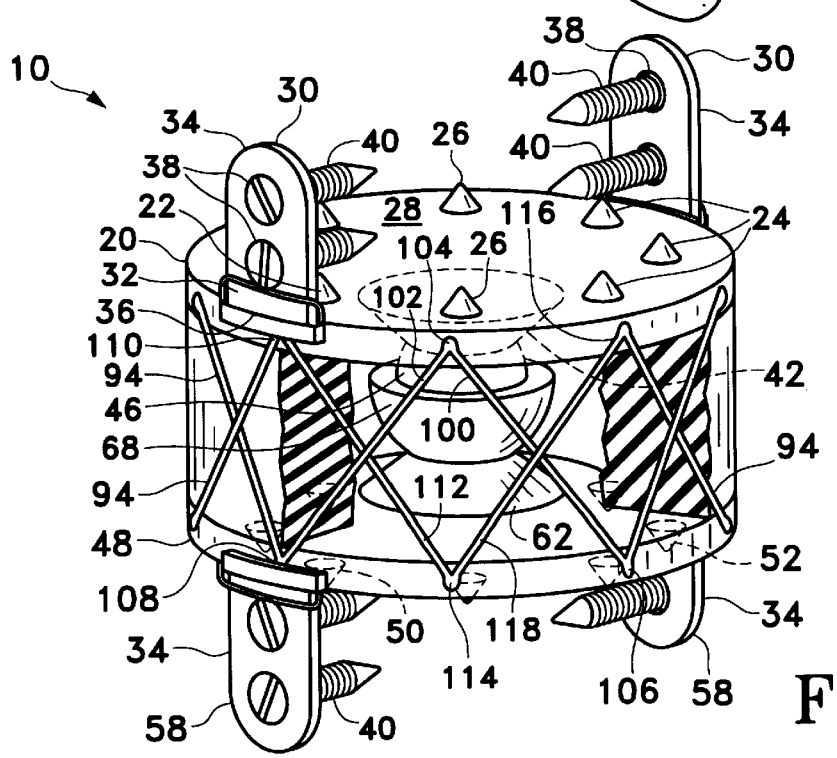
FIG. 2 is a perspective view of the vertebral body prosthesis of FIG. 1.
Figure 3:
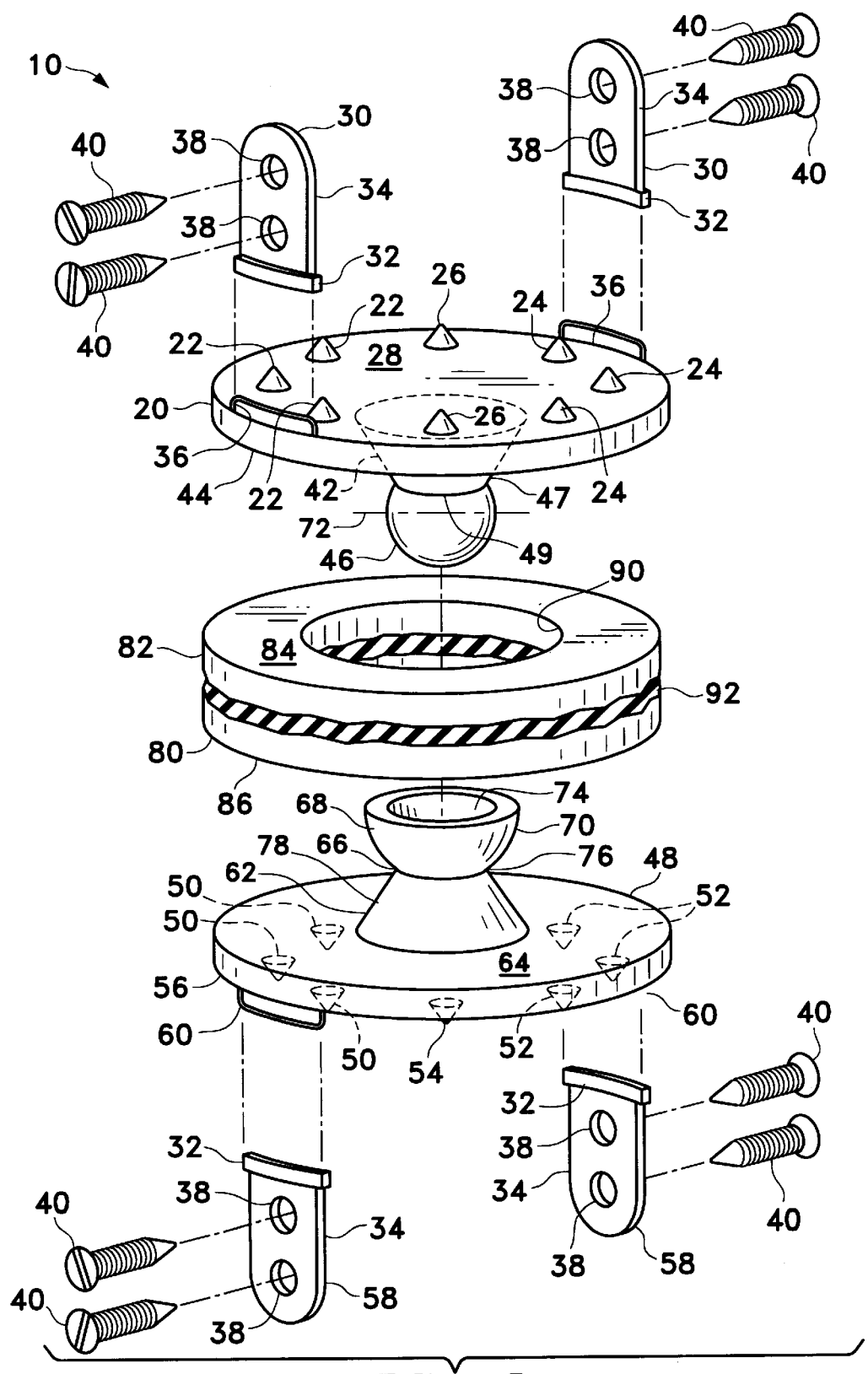
FIG. 3 is a an exploded perspective view of the vertebral body prosthesis of FIG. 1.

Referring to FIGS. 1–3, the vertebral body prothesis 10, includes an upper plate member 20 having a left-hand side group of three upwardly projecting fine needle-like spikes 22 arranged in a triangle, a right-hand side group of three upwardly projecting fine need-like spikes 24 arranged in a triangle, and a pair of circumferential upwardly projecting fine needle-like spikes 26 lying across a diameter of the upper plate member 20 in along a centerline between the groups of spikes 22, 24, all formed on the upper surface 28 of the upper plate member 20. A pair of opposed interchangeable upwardly projecting upper anchoring plates 30 each includes a base portion 32 that is wider and thicker than the bracket body 34, and which is fixed by welding or the like into an anchoring loop 36 fastened along the circumference of the upper plate member 20 by welding or the like. Each anchoring plate 30 includes a pair of vertically spaced screw apertures 38, each of which receives a bone screw 40, which is screwed into the upper disc 16. A downwardly projecting upper truncated cone member, or depending ball supporting member, 42 is fixed to a lower surface 44 of the upper plate member 20 at its center such that the centers of the upper plate member 20 and the upper truncated cone member are superposed. The widest portion of the upper truncated cone member 42 is fixed to the lower surface 44 of the upper plate member 20. A depending ball 46 is attached to or integrally formed with, the lower portion 47 of the upper truncated cone 42. The ball member 46 comprises a sphere with the top 20–35% removed, resulting in a straight line 49 plane or joiner with the cone member 42.

Still referring to FIGS. 1–3, the lower plate member 48 has left-hand side group of three downwardly projecting fine needle-like spikes 50 arranged in a triangle, a right-hand side group of three downwardly projecting fine need-like spikes 52 arranged in a triangle, and a pair of circumferential downwardly projecting fine needle-like spikes 54 lying across a diameter of the lower plate member 48 in along a centerline between the groups of spikes 50, 52 all formed on the lower surface 56 of the lower plate member 48. A pair of opposed lower anchoring plates 58 project downwardly and a fixed by welding or the like in lower anchoring loops 60 fixed in the lower plate member 48 adjacent to its circumference by welding or the like. In construction, installation and use, the lower anchoring plates 58 are interchangeable with the upper anchoring plates 30 and discussion and reference characters pertaining to the upper anchoring plates 30 also apply to the lower anchoring plates 58. The lower anchoring plates 58 lie across a diameter of the lower plate member 48, i.e., are opposed, and are vertically aligned with the upper anchoring plates 30, which lie across the corresponding diameter of the upper plate member 20 in the preferred embodiment. This results in an upper anchoring plate 30 on the right-hand side of the vertebral body prosthesis 10 and another on the left-hand side of the vertebral body prosthesis 10 and in both cases the upper anchoring plates 30 are in the middle of the sides so as to maximize their purchase on the vertebral bodies 12, 14 and the lower anchoring plates 58 are directly below the upper anchoring plates 30. If the circle of the upper plate member 20 and the lower plate member 48 are considered as a twelve hour clock face with the twelve o'clock position at the farthest point away from the viewer in FIGS. 1–3, the anchoring plates 30, 58 are at 3:00 O'clock and 9:00 O'clock. In an alternative embodiment, the anchoring plates 30, 58 may be moved forward to about the 10:00 O'clock position or backward to about the 2:00 O'clock position.

Figure 4:
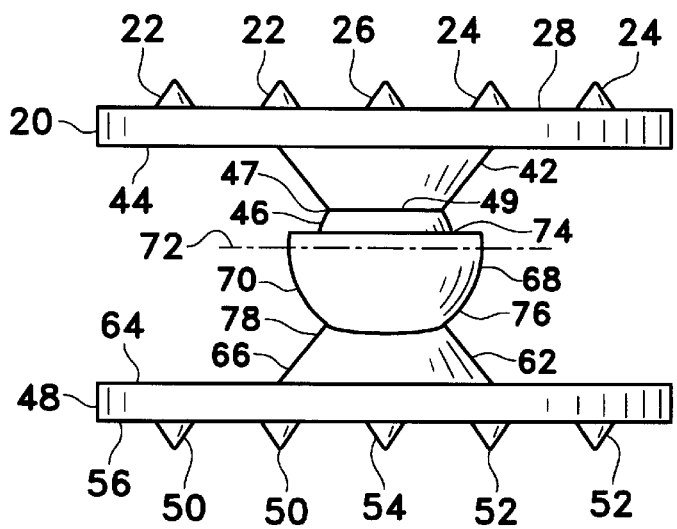
FIG. 4 is side elevation of the ball and socket arrangement and upper and lower plate of the vertebral body prosthesis of FIG. 1.
Figure 5:
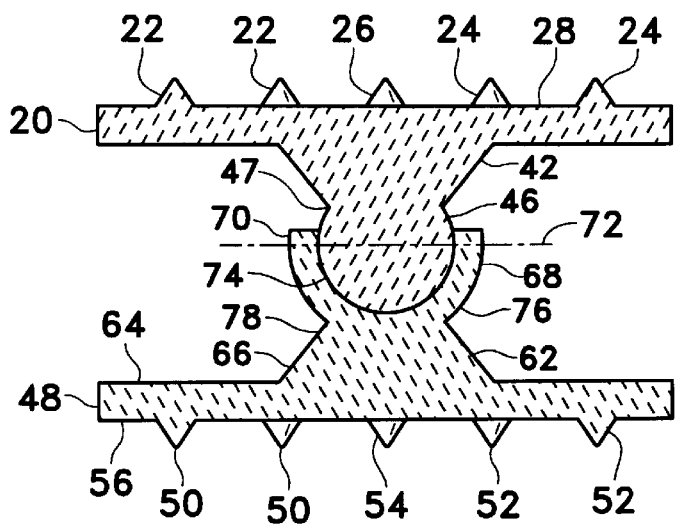
FIG. 5 is a cross sectional side elevation of the apparatus of FIG. 4.

An upwardly projecting lower truncated cone member, or upstanding socket supporting member, 62 is attached to or integrally formed with, the upper surface 64 of the lower plate member 48. The wider end of the cone member 62 is adjacent to the lower plate member 48 and the center of the cone member 62 is located at the center of the plate member 48, so that these centers are superposed. At the upper, or narrow, end 66 of the lower truncated cone member 62 is a cup socket 68 having side walls 70 for receiving the ball member 46. As best seen in FIGS. 4, 5, the side walls 70 of the cup socket 68 extend upwardly beyond the diameter 72 of the ball 46, reducing the chances that the ball 46 will be forced from the cup socket 68. The outer surface of the cup socket 68 is basically spherical in shape, although it could be any shape, and the interior socket portion 74 is a spherical socket designed to receive and mate with the ball 46 in close tolerance. A lower portion 76 of the cup socket 68 is flattened where it joins the upper end 78 of the lower truncated cone member 62.

The ball 46 and cup socket 68 arrangement fit and lock into each other and prevent radial movement, but facilitate axial rotational movement The upper and lower plate members 20, 48 can rotate about a vertical axis, and tilt at basically any angle through about 45–75% relative to the vertical throughout the full rotation, but cannot be compressed. A doughnut-shaped toroidal disc cushion 80 includes a circular outer side wall 82 perpendicular to a flat top wall 84 and to a flat bottom wall 86. A central aperture 90 accommodates the structures between the upper and lower plate members 20, 48. The disc cushion 80 is made of an elastic resilient material such as rubber, silicon, and includes reinforcing fibers 92. The disc cushion 80 limits tilting movement between the upper and lower plate members 20, 48 to a few degrees and cushions them, but does not bear a great deal of the forces of the spine in ordinary activities. Most of the of the forces in the spine are borne by the upper and lower plate members 20, 48, the ball 46 and cup socket 68, and the upper and lower truncated cone members 42, 62.

Referring to FIGS. 1, 2, to limit excessive relative rotation of the upper and lower plate members 20, 48, which are superposed when assembled, relative to a vertical axis through the center of the upper and lower plate member 20, 48, fine stainless steel limiting wires 94 are attached to the perimeters of the upper and lower plate members 20, 48 in such a fashion as to result in X-shaped reinforcing structures about the entire perimeter of the upper an lower plates 20, 48. More specifically, a wire 100 and a wire 102 are connected to the upper plate at a point 104. The wire 100 runs downward toward the right to its attachment point 106 on the perimeter of the lower plate member 48, while the wire 102 runs downwardly to the left to its attachment point 108 on the lower plate member 48. From an attachment point 110 on the upper plate member 20, a wire 112 runs downward to the left to the attachment point 114 on the perimeter of the lower plate member 48, while the wire 118 runs upwardly to the right from the same connection point 114 to an upper connection point 116 on the upper plate member 20. This pattern is repeated about the perimeter of both the upper and lower plate members 20, 48 (regardless of the plan view shape of the plate members), to provide a repeating X pattern of the limiting wires 94.

Figure 6:
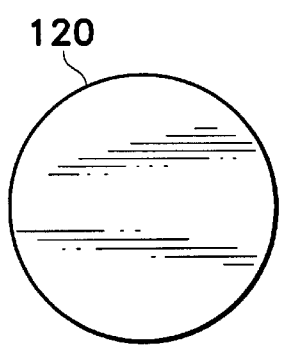
FIG. 6 is a top plan view of the upper and lower plate assembly illustrating the preferred circular shape of these members.
Figure 7:
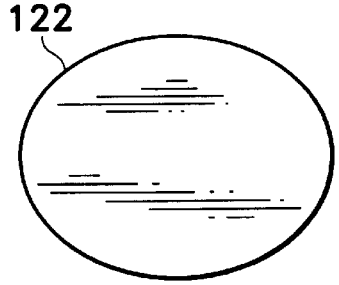
FIG. 7 is a top plan view of an alternative embodiment of the upper and lower plate assemble having an oval shape.
Figure 8:
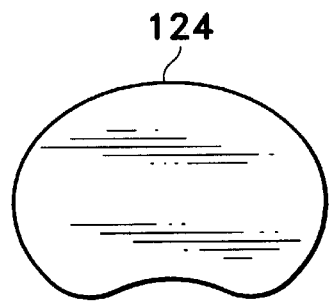
FIG. 8 is a top plan view of another alternative embodiment of the upper and lower plate assembly having a kidney shape.

Referring now to FIG. 6 the overall plan view of either or both upper and lower plate members 20, 46 is the circular disc 120 is a circle. As shown in FIGS. 7, 8, in alternative embodiments the overall plan view of both upper and lower plate members 20, 48 can be the oval plate member 122 or the kidney-shaped plate member 124, respectively.

The disc cushion 80 is inserted between the upper and lower plate members 20, 48 prior to assembly. Then the ball 46 is press fitted into the interior socket portion of the cup socket 68. The upper and lower plate members 20, 48, may be made of metal and in this case, the limiting wires 94 are welded on the plates 20, 48, the truncated cone members 42, 62, and the ball 46 and cup socket 68 may also be made of metal and are welded to the upper and lower plate members 20, 48. All the spikes are also made of metal and are welded onto the plate members 20, 48, as are the anchoring plates 30. Alternatively, each plate member 20, 48 and all spikes, truncated cones, the ball and the socket, can be made in one piece from ceramic materials. In this case, the anchoring plates 30 are fixed into the bracket slots and the wires are fastened to the plates by an adhesive. The upper and lower truncated cones 42, 62 respectively may be any desired shape adequate to support the associated ball 46 and cup socket 68.

While the present invention has been described in accordance with the preferred embodiments thereof, the description is for illustration only and should not be construed as limiting the scope of the invention. Various changes and modifications may be made by those skilled in the art without departing from the spirit and scope of the invention as defined by the following claims.

I claim:

1. A vertebral body prosthesis comprising:
   a. an upper plate having a depending ball supporting member comprising a truncated cone member projecting downwardly from said plate and having a narrower end lower than a wider end, with said lower end terminating in a depending ball portion;
   b. a lower plate having an upstanding hemispherical socket supporting member having an upper end connected to a hemispherical socket, with said ball seated in said socket; and
   c. a resilient toroidal disc interposed between said upper plate and said lower plate.

2. A vertebral body prosthesis in accordance with claim 1 further comprising a plurality of upwardly projecting spikes on an upper surface of said upper plate and a plurality of downwardly projecting spikes on a lower surface of said lower plate.

3. A vertebral body prosthesis in accordance with claim 1 further comprising a plurality of upwardly projecting anchoring brackets fastened to a perimeter of said upper plate, wherein each said bracket comprises an elongated bracket member having two vertically aligned apertures for receiving anchoring fasteners and said bracket member further comprises a thickened lower section for securing said bracket member in an anchoring loop fastened to said upper plate.

4. A vertebral body prosthesis in accordance with claim 1 further comprising a plurality of downwardly projecting anchoring brackets fastened to a perimeter of said lower plate, wherein each said bracket comprises an elongated bracket member having two vertically aligned apertures for receiving anchoring fasteners and said bracket member further comprises a thickened upper section for securing said bracket member in an anchoring loop fastened to said lower plate.

5. A vertebral body prosthesis in accordance with claim 1 wherein said socket comprises an upper edge and said upper edge extends upwardly above the diameter of said depending ball.

6. A vertebral body prosthesis in accordance with claim 1, further comprising a plurality of wires fastened to said upper plate and to said lower plate, wherein said wires form a repeating X pattern about the perimeter of said upper plate and said lower plate, wherein each X comprises an two upper arms, each said arm having an upper end, and two lower arms, each said arm having a lower end, and each upper end of each said upper arm is connected to an upper arm of an adjoining X and each said lower end of each said lower arm is connected to a lower arm of an adjoining X and said upper and lower ends are fastened to an edge of said upper plate or said lower plate.

7. A vertebral body prosthesis in accordance with claim 1 wherein said resilient toroidal disc comprises a layer of reinforcing fibers.

8. A vertebral body prosthesis in accordance with claim 1 further comprising a plurality of anchoring loops connected to said upper plate and a plurality of anchoring loops connected to said lower plate, wherein each said anchoring loop comprises a wire loop fastened to one said upper or said lower plate for receiving an anchoring bracket, which is retained in said anchoring loop by a thickened end portion of each said anchoring bracket.

9. A vertebral body prosthesis comprising:
   a. an upper plate having a depending ball supporting member comprising a truncated cone member projecting downwardly from said plate and having a narrower end lower than a wider end, with said lower end terminating in a depending spherical ball portion;
   b. a lower plate having an upstanding hemispherical socket supporting member comprising a truncated cone having a narrower end and a wider end, with said wider end connected to said lower plate, said socket supporting member having an upper end connected to a hemispherical socket, with said ball seated in said socket; and
   c. a toroidal disc interposed between said upper plate and said lower plate; and
   d. a plurality of wires arrayed in a repeating X pattern, each said wire having one end connected to said upper plate and a second end connected to said lower plate.

10. A vertebral body prosthesis in accordance with claim 9 further comprising a plurality of upwardly projecting spikes connected to an upper surface of said upper plate and a plurality of downwardly projecting spikes connected to a lower surface of said lower plate.

11. A vertebral body prosthesis in accordance with claim 9 further comprising a repeating X pattern formed by said wires, wherein each X comprises two upper arms, each said arm having an upper end, and two lower arms, each said arm having a lower end, and each upper end of each said upper arm is connected to an upper arm of an adjoining X and each said lower end of each said lower arm is connected to a lower arm of an adjoining X.

12. A vertebral body prosthesis in accordance with claim 9 wherein said toroidal disc comprises a doughnut-shaped toroidal disc cushion further comprising an upper elastic resilient member and a lower elastic resilient member and a plurality of reinforcing fibers between said upper and lower elastic resilient members.

* * * * *